(12) United States Patent
Patterson et al.

(10) Patent No.: US 10,653,354 B2
(45) Date of Patent: May 19, 2020

(54) MEDICAL TESTING APPARATUS AND METHOD OF USE

(71) Applicants: THE RESEARCH INSTITUTE AT NATIONWIDE CHILDREN'S HOSPITAL, Columbus, OH (US); Ohio State Innovation Foundation, Columbus, OH (US); Benjamin A. Patterson, Findlay, OH (US); Jay A. Shepherd, Columbus, OH (US)

(72) Inventors: Amber M. Patterson, Findlay, OH (US); Benjamin A. Patterson, Findlay, OH (US); Jay A. Shepherd, Columbus, OH (US); Meagan W. Shepherd, Columbus, OH (US)

(73) Assignees: Research Institute at Nationwide Children's Hospital, Columbus, OH (US); Ohio State Innovation Foundation, Columbus, OH (US)

( * ) Notice: Subject to any disclaimer, the term of this patent is extended or adjusted under 35 U.S.C. 154(b) by 1282 days.

(21) Appl. No.: 14/777,370

(22) PCT Filed: Mar. 12, 2014

(86) PCT No.: PCT/US2014/024355
§ 371 (c)(1),
(2) Date: Sep. 15, 2015

(87) PCT Pub. No.: WO2014/150833
PCT Pub. Date: Sep. 25, 2014

(65) Prior Publication Data
US 2016/0030114 A1 Feb. 4, 2016

Related U.S. Application Data

(60) Provisional application No. 61/787,336, filed on Mar. 15, 2013, provisional application No. 61/844,474, filed on Jul. 10, 2013.

(51) Int. Cl.
*A61B 5/00* (2006.01)
*A61B 50/30* (2016.01)

(52) U.S. Cl.
CPC .......... *A61B 5/411* (2013.01); *A61B 50/3001* (2016.02)

(58) Field of Classification Search
CPC ........................... A61B 5/411; A61B 50/3001
See application file for complete search history.

(56) References Cited

U.S. PATENT DOCUMENTS

| 1,798,729 A | 3/1931 | Divekey |
| 2,819,668 A | 1/1958 | Mcaneny |

(Continued)

FOREIGN PATENT DOCUMENTS

GB        100633 A        6/1916

OTHER PUBLICATIONS

One page photograph of a device shown or publicly displayed more than one year prior to the filing date of subject application, namely Jan. 15, 2012.

(Continued)

*Primary Examiner* — Rene T Towa
(74) *Attorney, Agent, or Firm* — Tarolli, Sundheim, Covell & Tummino LLP; John A. Yirga, Esq.

(57) ABSTRACT

A medical testing apparatus and method of use for for penetrating a patient's tissue with an agent, the apparatus comprises an arcuate rail having spaced first and second sides supported by upper and lower arcuate surfaces and an arcuate handle having first and second ends extending from the upper surface of the arcuate rail. A plurality of tips extend substantially from and normally outward as the lower arcuate surface. The plurality of tips comprises alternating blunt tips and reed tips.

20 Claims, 18 Drawing Sheets

(56) References Cited

U.S. PATENT DOCUMENTS

| | | | |
|---|---|---|---|
| 3,556,080 A | 1/1971 | Hein | |
| 3,675,766 A * | 7/1972 | Rosenthal | A61B 17/205 |
| | | | 206/367 |
| 3,955,233 A | 5/1976 | Nakamura | |
| 4,183,353 A | 1/1980 | Gallub | |
| 4,809,707 A | 3/1989 | Kraft et al. | |
| 5,044,372 A | 9/1991 | Anhauser et al. | |
| D322,673 S | 12/1991 | Muller | |
| 5,139,029 A * | 8/1992 | Fishman | A61B 5/411 |
| | | | 600/556 |
| 5,179,959 A | 1/1993 | Fishman et al. | |
| D340,289 S | 10/1993 | Gerber | |
| 5,547,555 A | 8/1996 | Schwartz et al. | |
| 5,692,518 A | 12/1997 | Baker et al. | |
| 5,733,269 A | 3/1998 | Fuisz | |
| 5,746,700 A * | 5/1998 | Hsiao | A61B 5/411 |
| | | | 600/556 |
| 5,749,836 A | 5/1998 | Hsiao | |
| D412,990 S | 8/1999 | Woolston et al. | |
| 6,024,706 A * | 2/2000 | Hsiao | A61B 10/0035 |
| | | | 600/556 |
| 6,095,046 A | 8/2000 | Lookholder et al. | |
| D439,985 S | 4/2001 | Sanner | |
| 6,319,467 B1 | 11/2001 | McLernon, III | |
| 6,475,160 B1 | 11/2002 | Sher | |
| 6,611,707 B1 | 8/2003 | Prausnitz et al. | |
| D491,276 S | 6/2004 | Langille | |
| 6,902,554 B2 | 6/2005 | Huttner | |
| D523,964 S | 6/2006 | Phelan et al. | |
| 7,344,499 B1 | 3/2008 | Prausnitz et al. | |
| D623,303 S | 9/2010 | Koivulehto et al. | |
| D629,517 S | 12/2010 | Jauch et al. | |
| D667,548 S | 9/2012 | Brannon | |
| D684,276 S | 6/2013 | Hudson et al. | |
| 8,597,199 B2 | 12/2013 | Harish et al. | |
| D698,937 S | 2/2014 | Laverack et al. | |
| D721,435 S | 1/2015 | Patterson et al. | |
| 2004/0236315 A1 | 11/2004 | Hered | |
| 2009/0247902 A1 | 10/2009 | Reichert et al. | |
| 2010/0022910 A1 * | 1/2010 | Lane | A61B 5/0059 |
| | | | 600/556 |
| 2010/0298784 A1 * | 11/2010 | Miller | A61B 10/025 |
| | | | 604/272 |
| 2012/0089048 A1 | 4/2012 | Harish et al. | |
| 2012/0253224 A1 | 10/2012 | Mir et al. | |
| 2013/0231583 A1 * | 9/2013 | Rekkerth | A61B 5/445 |
| | | | 600/556 |
| 2013/0289440 A1 * | 10/2013 | Hein, Jr. | A61B 5/411 |
| | | | 600/556 |

OTHER PUBLICATIONS

International Search Report and Written Opinion of the International Searching Authority dated Jul. 9, 2014 for International Application No. PCT/US14/24355 (21 pages).

Quintest Multiple Skin Test System Ad. of a device shown or publicly displayed more than one year prior to the filing date of subject application, namely Jan. 15, 2012 (4 pages).

\* cited by examiner

MEDICAL TESTING APPARATUS AND METHOD OF USE

CROSS REFERENCES TO RELATED APPLICATIONS

The present application is a 35 U.S.C. § 371 National Stage Patent Application of International PCT Application Serial Number PCT/US2014/024355 having an International filing date of 12 Mar. 2014 and that was published on 24 Sep. 2014 under international publication number WO 2014/150833, which claims priority to U.S. Provisional Application Ser. No. 61/1787,336 that was filed on 15 Mar. 2013 and U.S. Provisional Application Serial No. 61/844,474 that was filed on 10 Jul. 2013. This Application claims priority to and incorporates by reference the above applications in their entirety for all purposes.

TECHNICAL HELD

The present disclosure relates to a medical testing apparatus and method of use, and more particularly, a medical testing apparatus for carrying a testing agent, the testing apparatus utilized in penetrating a patient's tissue during a medical procedure, the testing apparatus further corresponding to a well or kit.

BACKGROUND

Various medical testing procedures require penetrating the patient's skin with a medical device such as a short needle-like lance, often to a depth less than the subcutaneous tissue layer. The lance typically carries a testing agent that may result in the reaction to the skin cells surrounding the penetrated region defined as the testing area.

The testing area is typically observed once the patient is exposed to the agent by the medical device for any reaction to the skin cells. If a reaction to the agent occurs, traumatized skin cells on the patient at the testing area become inflamed and are often no larger than two or three centimeters. For some patients, it is possible for the skin reaction to take fifteen to twenty minutes.

Conventional allergy testing often referred to as a prick test similarly uses a single lance carrying an allergen that penetrates a testing area in order to release the allergen into the patient's skin. The testing area is then monitored for a period of time to see if any traumatized skin cells are generated, thus providing a visible allergic reaction.

SUMMARY

One example embodiment includes a medical testing apparatus for penetrating a patient's tissue with an agent, the apparatus comprises an arcuate rail having spaced first and second sides supported by upper and lower arcuate surfaces and an arcuate handle having first and second ends extending from the upper surface of the arcuate rail. A plurality of tips extend substantially from, and normally outward of the lower arcuate surface. The plurality of tips comprise alternating blunt tips and reed tips.

Another example embodiment includes a method of performing a medical testing procedure on a patient. The method comprises the steps of grasping either an arcuate rail having spaced first and second sides supported by upper and lower arcuate surfaces or an arcuate handle having first and second ends extending from the upper surface of the arcuate rail and contacting a patient's tissue with a plurality of tips extending substantially from and normally away from the lower arcuate surface, the plurality of tips comprising alternating blunt tips and reed tips.

While another example embodiment comprises a medical testing apparatus for penetrating a patient's tissue with an agent. The apparatus comprises a rail having spaced first and second sides supported by upper and lower surfaces; a handle having first and second ends extending from the upper surface of the rail; and a plurality of blunt and reed tips extending substantially from and normally away from the lower surface, the plurality of blunt and reed tips spaced along the lower surface such that at least one but no more than three total tips of the plurality of blunt and reed tips contact a patient's tissue at any given time during use.

Another example embodiment includes a medical kit used for contacting a patient's tissue with an fluid. The medical kit comprises a medical testing apparatus having: an arcuate rail comprising spaced first and second sides supported by upper and lower arcuate surfaces; an arcuate handle having first and second ends extending from the upper surface of the arcuate rail; and a plurality of blunt and reed tips extending substantially from and normally away from the lower arcuate surface in a spaced relationship; a base having a cradle for supporting at least one medical testing apparatus, the cradle further comprising a well having a plurality of recesses for storing and supplying fluid to at least one of the blunt tips and the reed tips for contacting a patient's skin during use.

Another aspect of the disclosure includes a medical testing apparatus for releasing a fluid to a patient's tissue. The apparatus comprises an arcuate rail having spaced first and second sides supported by upper and lower arcuate surfaces; an arcuate handle having first and second ends extending from the upper surface of the arcuate rail; and a plurality of tips extending substantially from and normally away from the lower arcuate surface, the plurality of tips being in a spaced relationship about the lower arcuate surface.

A medical testing apparatus for releasing a fluid to a patent's tissue. The apparatus comprises: first and second arcuate rails having spaced first and second sides supported by upper and lower arcuate surfaces; a handle having first and second ends bisecting and coupled to the upper surface of the arcuate rails; and a plurality of tips extending substantially from and normally away from the lower arcuate surfaces of the first and second arcuate rails, the plurality of tips being in a spaced relationship about the lower arcuate surface.

BRIEF DESCRIPTION OF THE DRAWINGS

The foregoing and other features and advantages of the present disclosure will become apparent to one skilled in the art to which the present invention relates upon consideration of the following description of the invention with reference to the accompanying drawings, wherein like reference numerals refer to like parts unless described otherwise throughout the drawings and in which.

DETAILED DESCRIPTION

Referring now to the figures generally wherein like numbered features shown therein refer to like elements throughout unless otherwise noted. The present disclosure relates to a medical testing apparatus and method of use, and more particularly, a medical testing apparatus for carrying a testing agent, the testing apparatus utilized in penetrating a patient's tissue during a medical procedure. While the illustrated example embodiment describes the medical testing apparatus' application of allergens/or antigens into the skin of a patient, it should be appreciated that other medical uses of applying fluids into a patient's tissue with the testing apparatus are within the spirit and scope of the present disclosure.

For the purposes of this specification, penetrating a patient's tissue is intended to include, but is not limited to, the patient's skin, epidermis, dermis, and subcutaneous layers. While the medical testing apparatus utilizes various allergens in the testing of patients for various allergic reactions, the testing apparatus may use other diagnostic or medical treatment agents without departing from the spirit and scope of the claimed disclosure.

Figure 1:
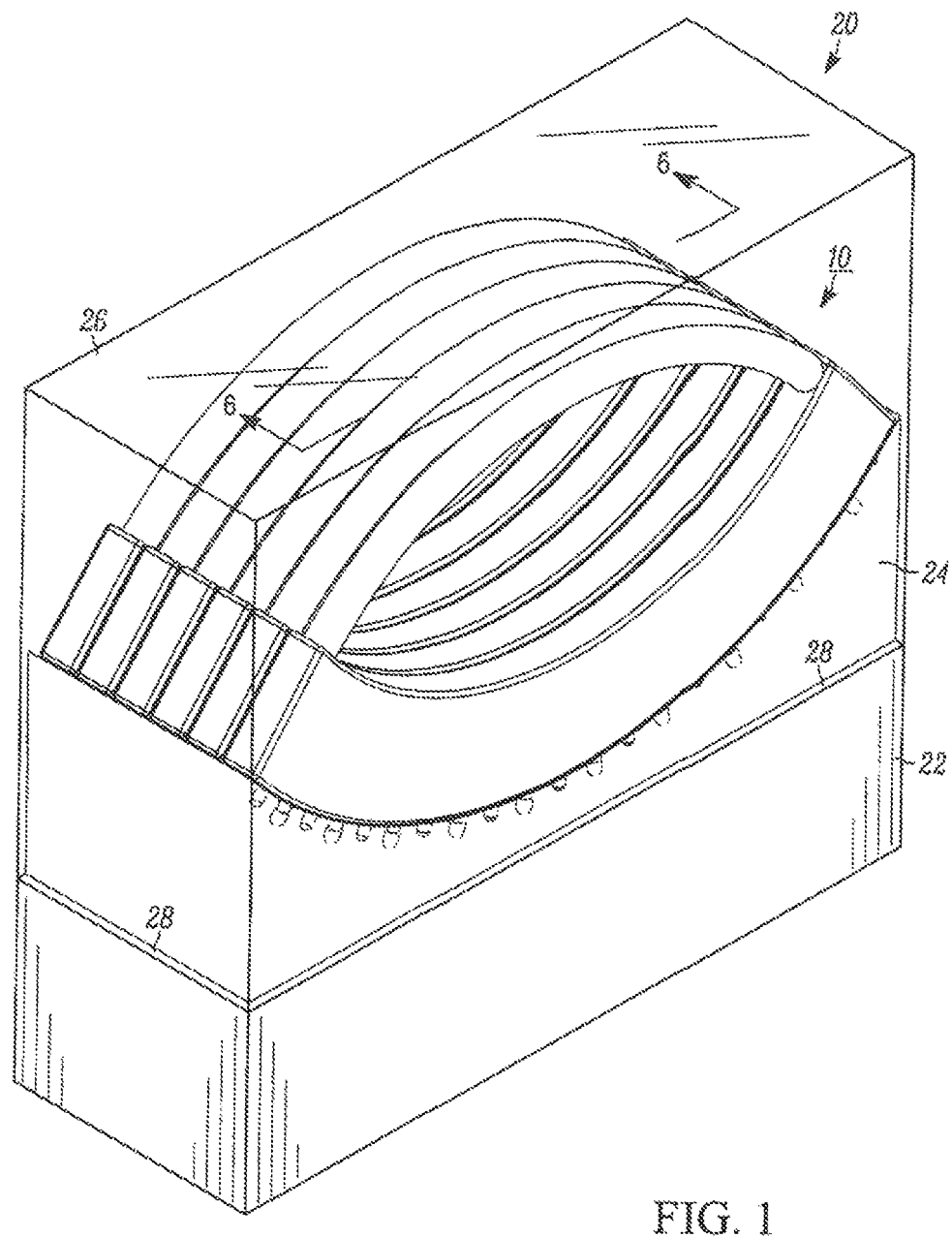
FIG. 1 is a perspective view of a plurality medical testing apparatuses positioned in a docking station, both constructed in accordance with one example embodiment of the present disclosure.

FIG. 1 illustrates a perspective view of a plurality of medical testing apparatuses 10 positioned in a docking station 20, both the testing apparatuses and docking station are constructed in accordance with one example embodiment of the present disclosure. The docking station 20 comprises a base 22, cradle 24, and cover 26. The docking station 20 is formed from molded plastic and the cover 26 in the illustrated example embodiment is transparent plastic, but could also be made of an opaque material as appreciated by those of ordinary skill in the art.

The cover 26 has the same dimensions as the base 22, but is slightly larger than the cradle 24, forming a peripheral self or recess 28 for carrying the cover. In the illustrated example embodiment, the docketing station 20 is constructed such that the testing apparatuses 10 are stationed in relatively close proximity (near contact) with each other, but could be expanded in size to include over an inch of space between each testing apparatus without departing from the spirit and scope of the claimed disclosure. The cover 26 provides protection to the testing apparatuses 10 and agent or fluids therein from the environment, debris, evaporation, or any combination thereof.

Figure 6:
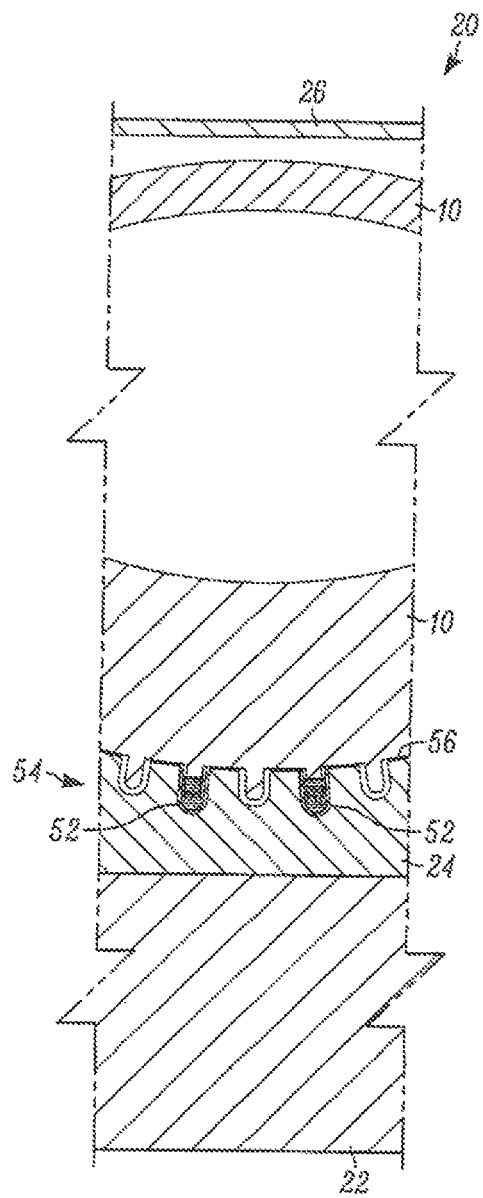
FIG. 6 is a section view of FIG. 1 along section lines 6-6.

FIG. 6 is a section view of the docking station 20 and one medical tester apparatus 10 illustrated FIG. 1 along section lines 6-6. The medical tester apparatus 10 includes an arcuate rail 12 having first and second sides 14 and 16, respectively, and an arcuate annular handle 18, having first and second ends, 17, and 19, extending from and above the arcuate rail. The arcuate rail 12 further comprises upper and lower arcuate surfaces, 30, 32, respectively spaced by first and second sides 14, and 16. First and second planer ends 34, 36, respectively of the arcuate rail 12 terminate the sides 14, 16 and surfaces 30, 32.

Figure 2:
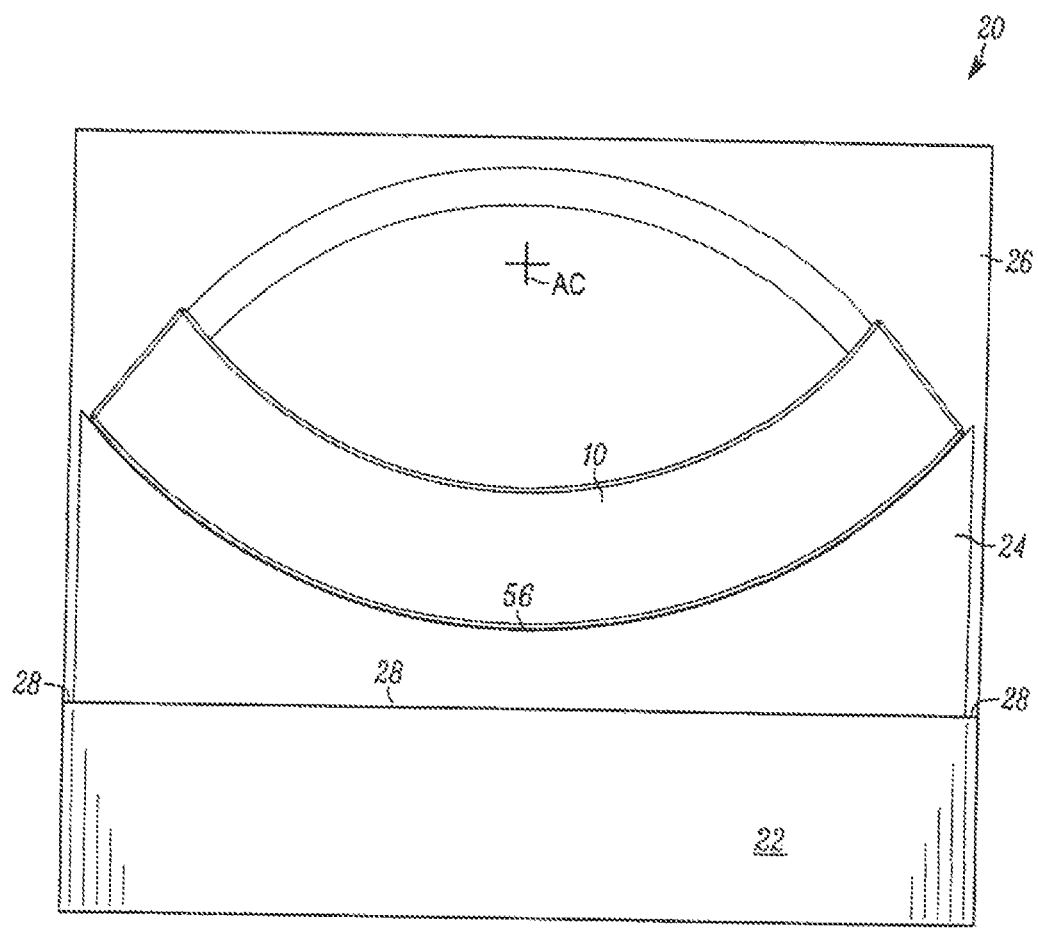
FIG. 2 is a front elevation view of FIG. 1.
Figure 3:
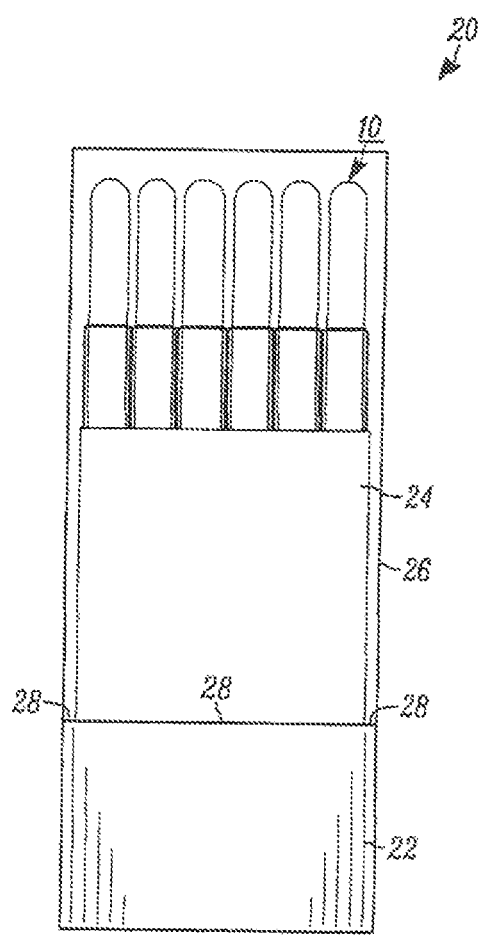
FIG. 3 is a side elevation view of FIG. 1.
Figure 4:
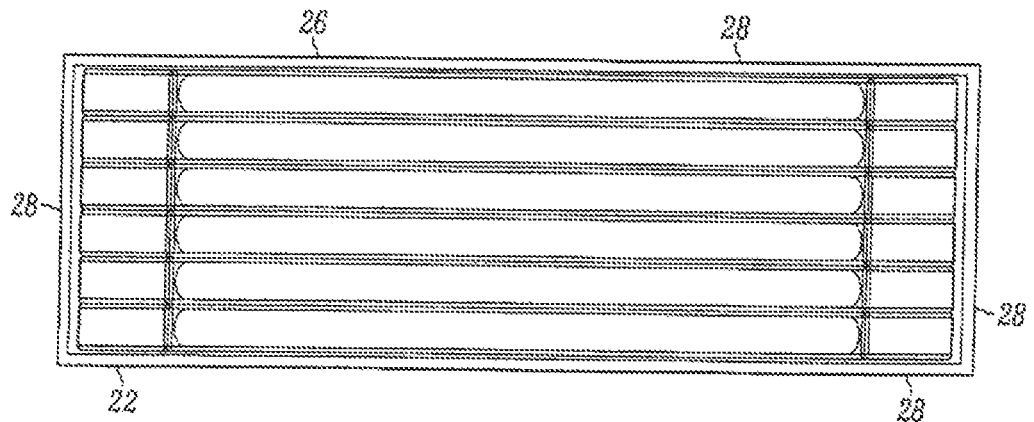
FIG. 4 is a top plan view of FIG. 1.
Figure 5:
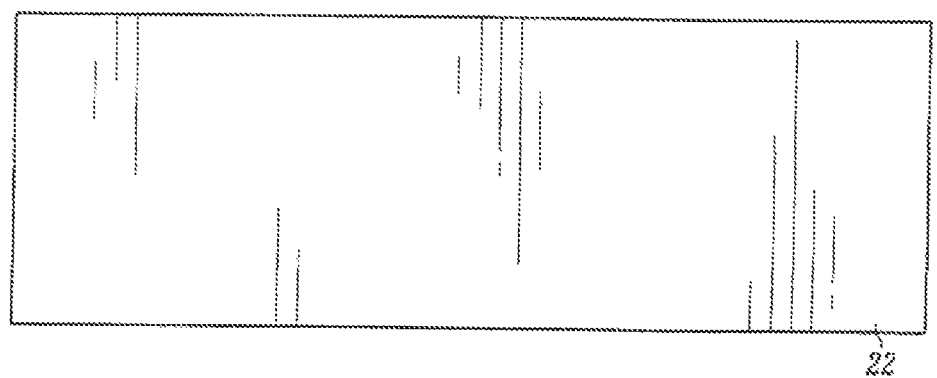
FIG. 5 is a bottom plan view of FIG. 1.

In the illustrated example embodiment, the arcuate rail 11 sides 14, 16, and surfaces 30, 32 share a common arcuate center "AC" as illustrated in FIG. 2. That is, the arcuate rail 12, skies 14, 16, and surfaces 30, 32 run parallel with each other about the arcuate center AC. In another example embodiment, the arc formed by the arcuate annular handle 18 and the arc formed by the arcuate rail 12 form an ogive, where their respective arcuate centers or centers of curvature lie within, outside, or on the other arc. In the illustrated example embodiment, the arc formed by the arcuate annular handle 18 and arcuate rail 12 form an equilateral ogive.

Projecting from, and as part of the arcuate rail 12 are a plurality of tips 40 that extend outward substantially orthogonally along the center of the lower arcuate surface 32 over the length of the arcuate rail 12. In one illustrated example embodiment, the plurality of tips alternate between a blunt tip 42 and a reed or a cannulus tip 44, such as FIGS. 8-15. It should be appreciated however that the order or arrangement of the blunt and reed tips can be in other combinations such as adjacent multiple blunt tips 42 alternating with a single reed tip 44 or adjacent multiple reed tips 44 alternating with a single blunt tip 42.

Figure 18:
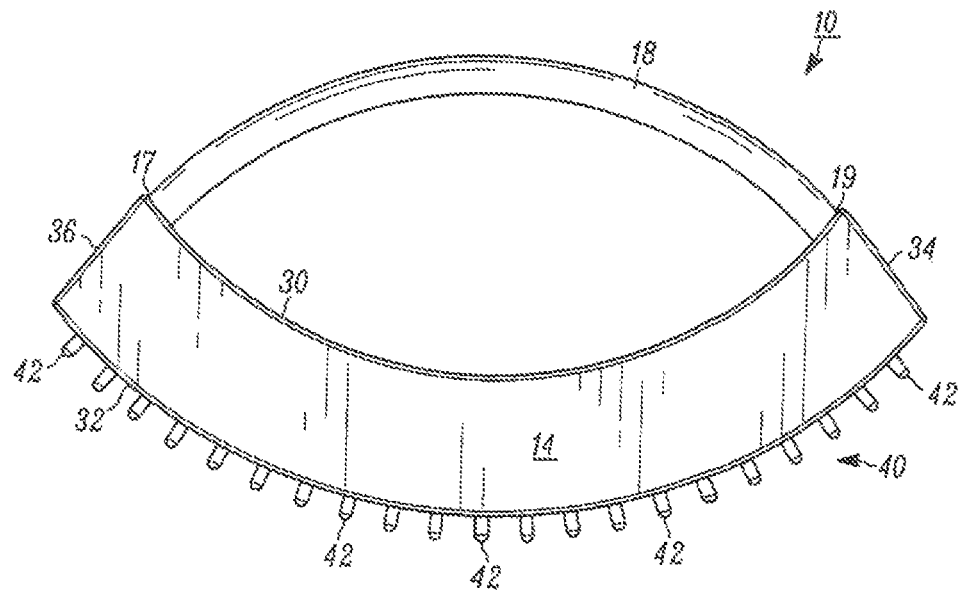
FIG. 18 is an elevation view testing apparatus constructed in accordance with one example embodiment of the present disclosure.

Illustrated in FIG. 18 is another example embodiment in which the testing apparatus 10 comprises only blunt tips 42. In this configuration, the testing device can be used for training medical professionals. Alternatively, the testing device 10 could be used as a marker by placing the blunt tips 42 into wells having fluid, such as ink. The ink is then applied to the patients skin by contacting each blunt tip 42 carrying ink against the patient's skin. This embodiment could further be used as a marking apparatus without ink by applying pressure to the apparatus in which the blunt tips 42 would leave for example, temporary indentations on the patient's skin, locating an area of interest for the medical practitioner.

Figure 19:
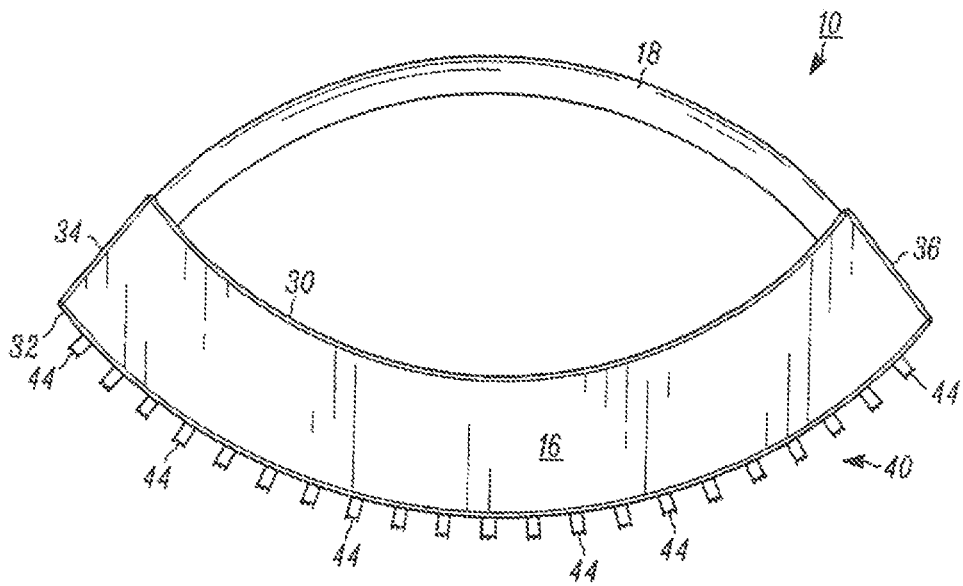
FIG. 19 is an elevation view of a testing apparatus constructed in accordance with one example embodiment of the present disclosure.

FIG. 19 illustrates another testing apparatus 10 constructed in accordance with one example embodiment of the present disclosure. The testing apparatus 10 comprises only reed tips 44 along the lower arcuate surface 32. The reed tip 44 includes one or more sharp points 46 for penetrating the patient's tissue. The reed tip 44 further comprises a cup-like cavity or cavity cup 48, forming a blind hole that produces a capillary effect when exposed to testing or treatment fluid 50, such as an allergen or antigen. For example, the fluid 50 is held in test tube reservoirs 52 that correspond to each reed tip 44. Upon insertion of the reed tip 44 into its corresponding test tube 52, the cavity cup 48 of the tip 44 becomes filled by a capillary action of the fluid 50. The fluid 50 transfers from the cavity cup 48 into the patient once the reed tip 44 passes through the patient's tissue. In another alternative example embodiment, the reed tips 44 are a multi-segmented to support both an extract portion and a portion for holding ink that would mark the patient's skin at the testing area.

Figure 20:
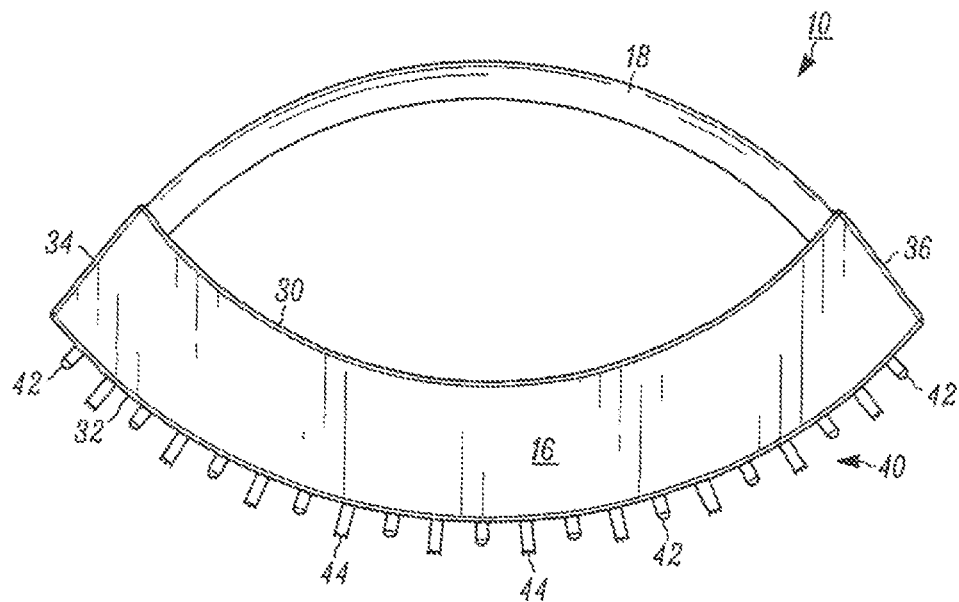
FIG. 20 is an elevation view of a testing apparatus constructed in accordance with one example embodiment of the present disclosure.

FIG. 20 illustrates yet another medical testing apparatus 10 constructed in accordance with one example embodiment of the present disclosure. The apparatus 10 includes alternating blunt 42 and reed tips 44, where the reed tips comprise a longer length or radial distance from the arcuate center AC of the lower arcuate surface 32, thus the reed tips 44 contact the patient's skin before any corresponding, i.e. adjacent blunt tips 42.

Figure 21:
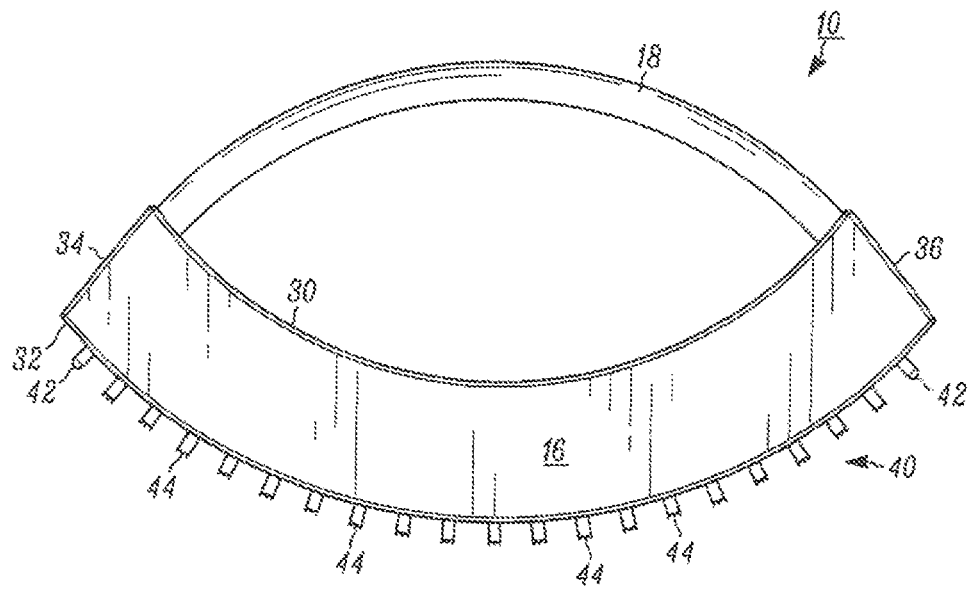
FIG. 21 is an elevation view of a testing apparatus constructed in accordance with one example embodiment of the present disclosure.

Illustrated in FIG. 21 is another example embodiment of a medical testing apparatus 10. The testing apparatus comprises only two blunt tips 42, located as the first and last tips along the lower arcuate surface 32. This would allow for ink or pressure marking by the blunt tip 42 to indicate the start and/or finish of the testing area on the patient's tissue. Thus, the blunt tips 42 act as an indicator of the area of interest that is tested on the patient.

Figure 16:
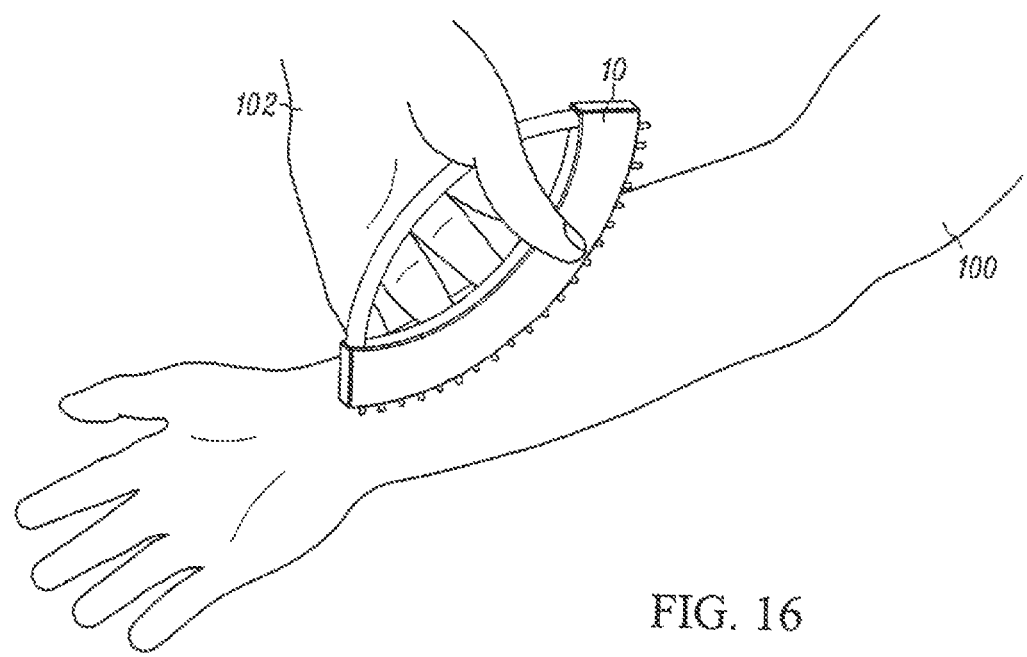
FIG. 16 is a perspective view of the medical testing apparatus in use at a starting position on a patent in accordance with the example embodiments of the present disclosure.
Figure 22:
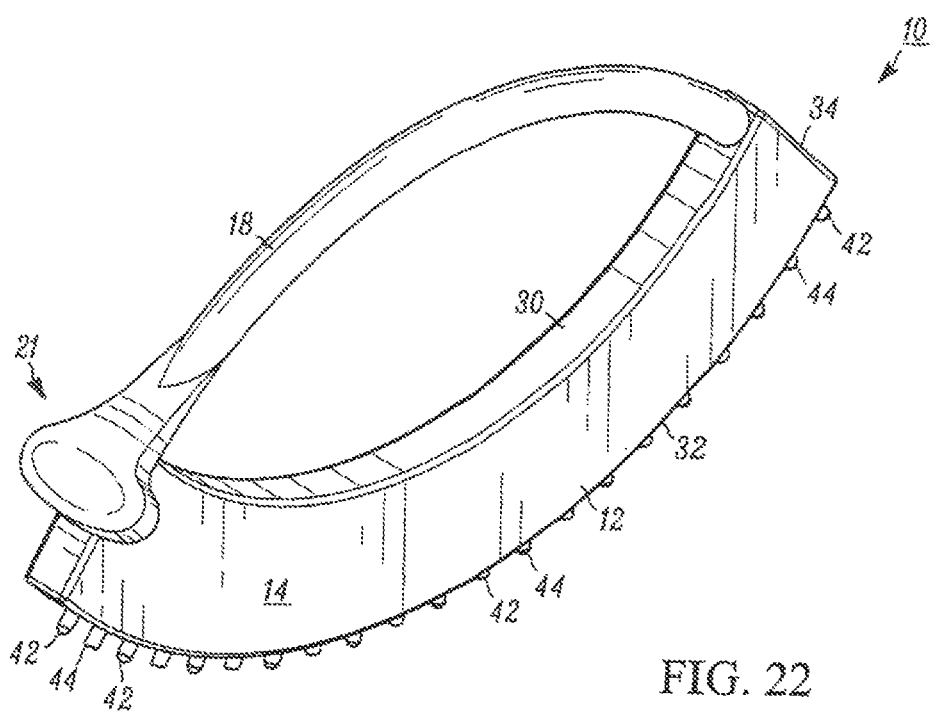
FIG. 22 is a perspective view of a testing apparatus constructed in accordance with one example embodiment of the present disclosure.

FIG. 22 illustrates a perspective view of a testing apparatus 10 constructed in accordance with another example embodiment of the present disclosure. The testing apparatus 10 comprises a thumb or finger support 21 extending from and molded into the handle 18. The thumb or finger support 21 provides an ergonomic rest for the operator's finger or thumb when the apparatus is rocked across the patient's tissue as illustrated in the orientation of FIG. 16 to the rocked position of FIG. 17. The thumb or finger support 21 allows for uniform pressure to both the apparatus 10 and patient, thus minimizing pain and discomfort.

In one example embodiment, the reed tips 44 are made from biomedical materials, such as biomedical plastic and/or biomedical metal suitable for inserting into a patient's skin. In the example embodiment the reed tips 44 are press-fit into corresponding openings 45 molded into the lower arcuate surface 32. This would allow the reed tips 44 to be purchased from a separate medical supplier, and replacement of the reed tips by a medical professional such as a nurse, doctor, or technician after each use. In an alternative example embodiment, the reed tips 44 are molded directly into the lower arcuate surface.

In the illustrated example embodiment of FIGS. 8-15, the entire testing apparatus 10, including the reed tips 44 is made from molded plastic, which is both inexpensive to manufacture and allows for the disposal of the testing apparatus after a single use. In the example embodiment, the blunt tips 42 and the reed tips 44 are molded directly into the lower arcuate surface 32. The spacing between the blunt tips 42 and reed tips 44 in the illustrated example embodiment is between one (1) and three (3) cm on the lower arcuate surface 32, allowing for sufficient viewing of reacting regions on the patient's skin. As well, the goal of the reed tips 44 is to be at least two (2) centimeters apart at the sharp points 46, where the points touch the surface of the patient's skin. In one example embodiment, no more than three (3) tips 42 and 44 collectively, touch the patient's skin at any given time, as further illustrated in FIG. 17.

Figure 7A:
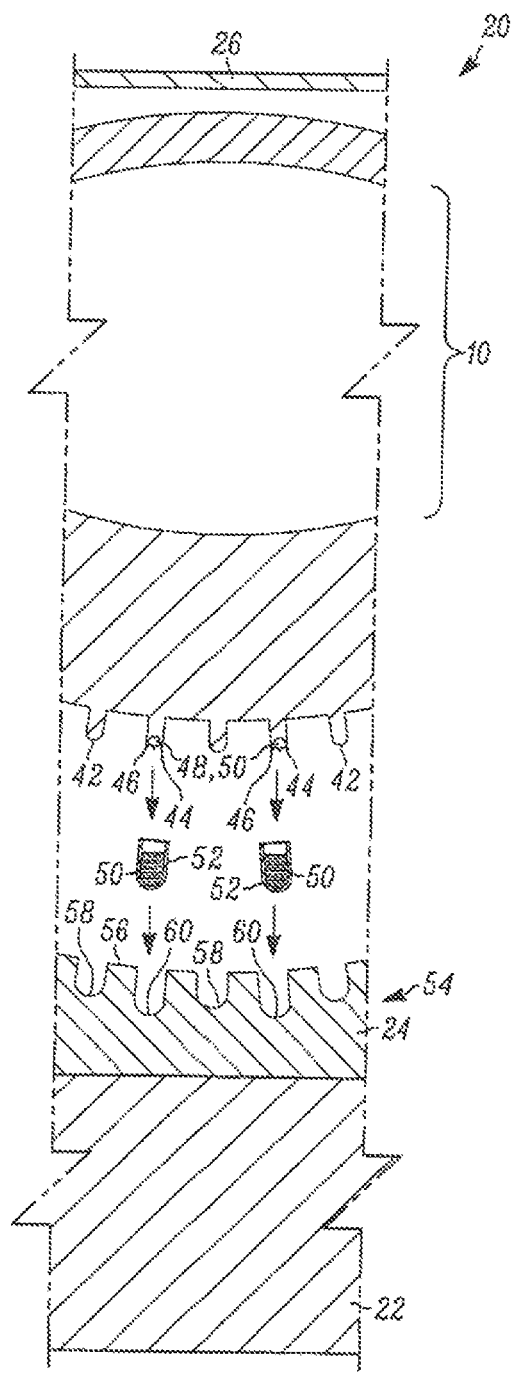
FIG. 7A is an exploded assembly view of the section view of FIG. 6 in accordance with one example embodiment.
Figure 7B:
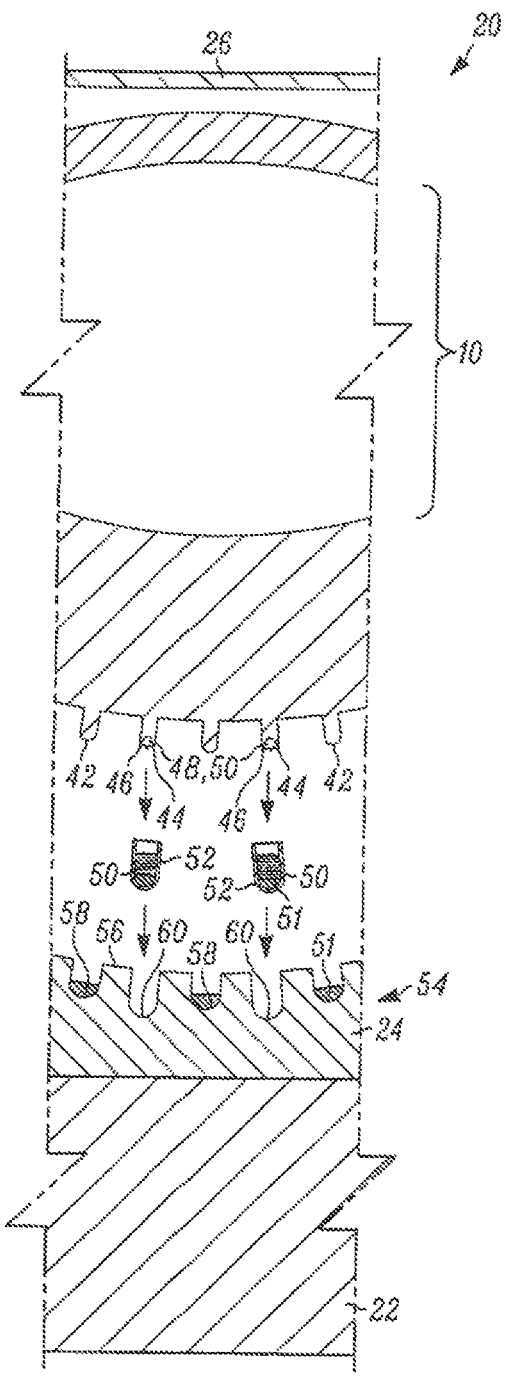
FIG. 7B is an exploded assembly view of the section view of FIG. 6 in accordance with another example embodiment.
Figure 8:
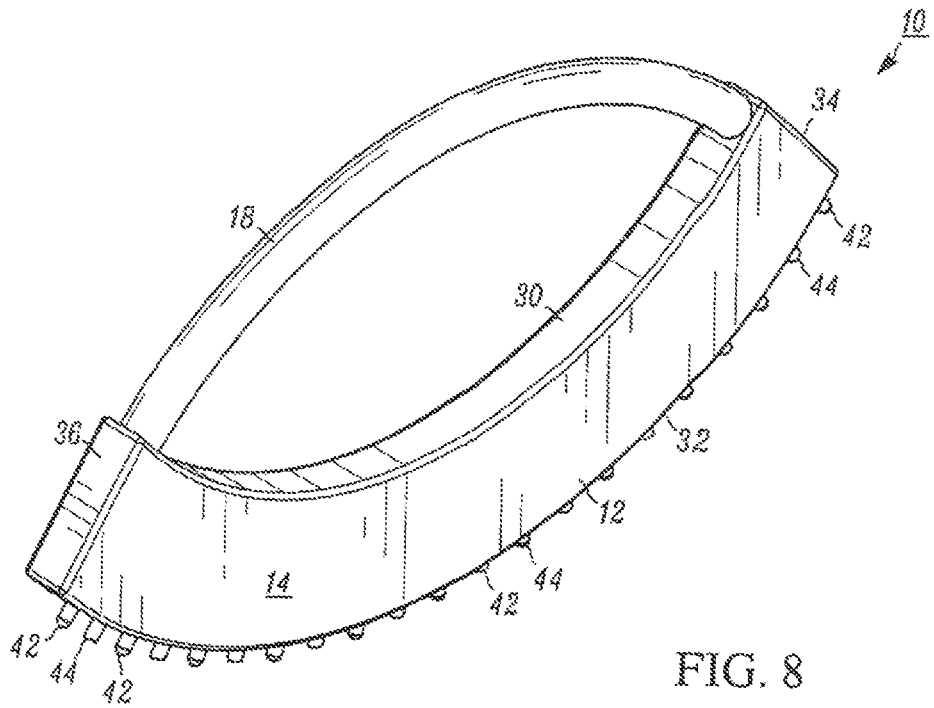
FIG. 8 is an upper perspective view of a medical testing apparatus constructed in accordance with one example embodiment of the present disclosure.
Figure 9:
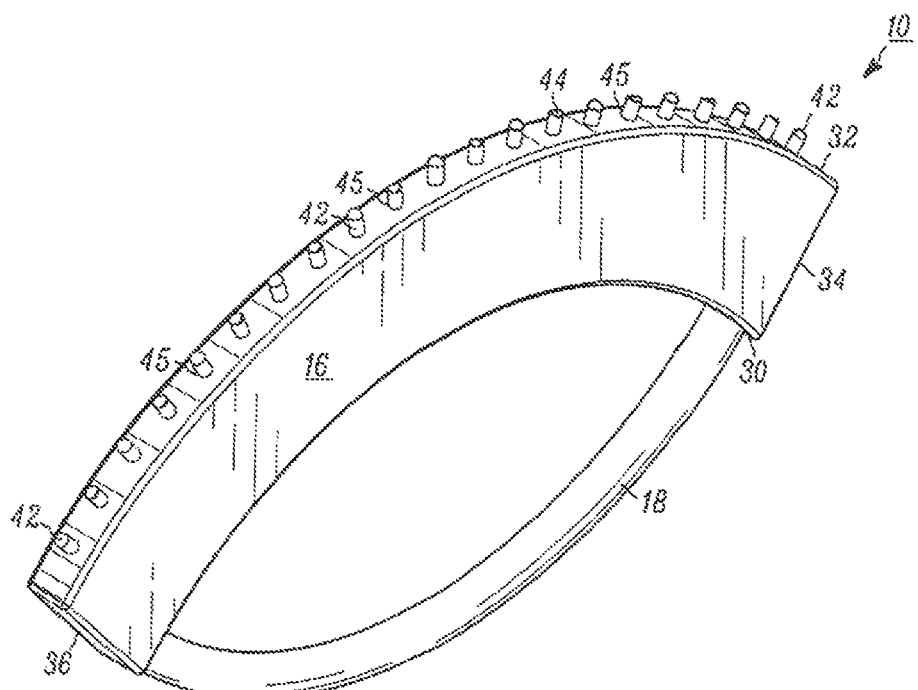
FIG. 9 is a lower perspective view of the medical testing apparatus of FIG. 8.
Figure 10:
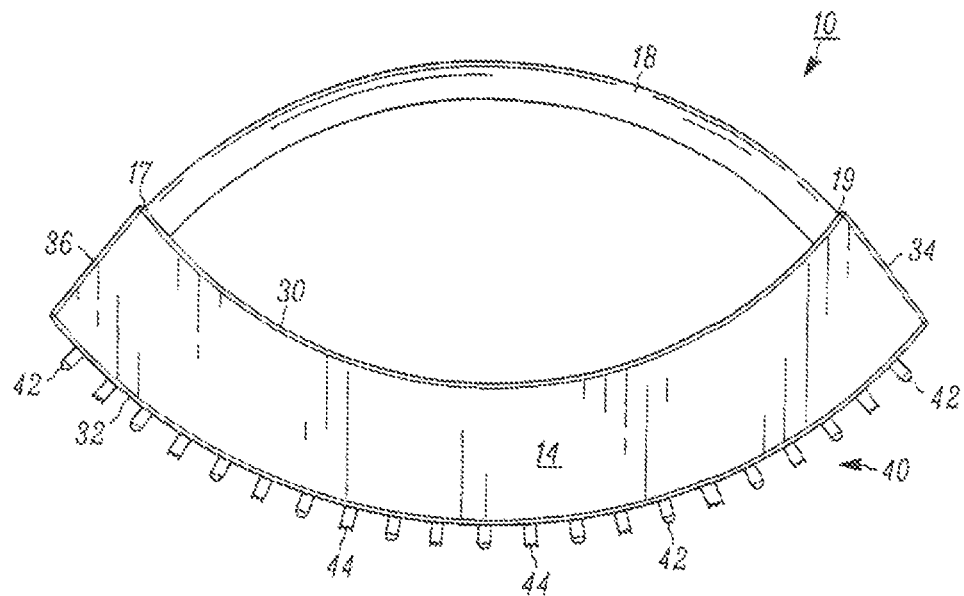
FIG. 10 is a front elevation view of the medical testing apparatus of FIG. 8.
Figure 11:
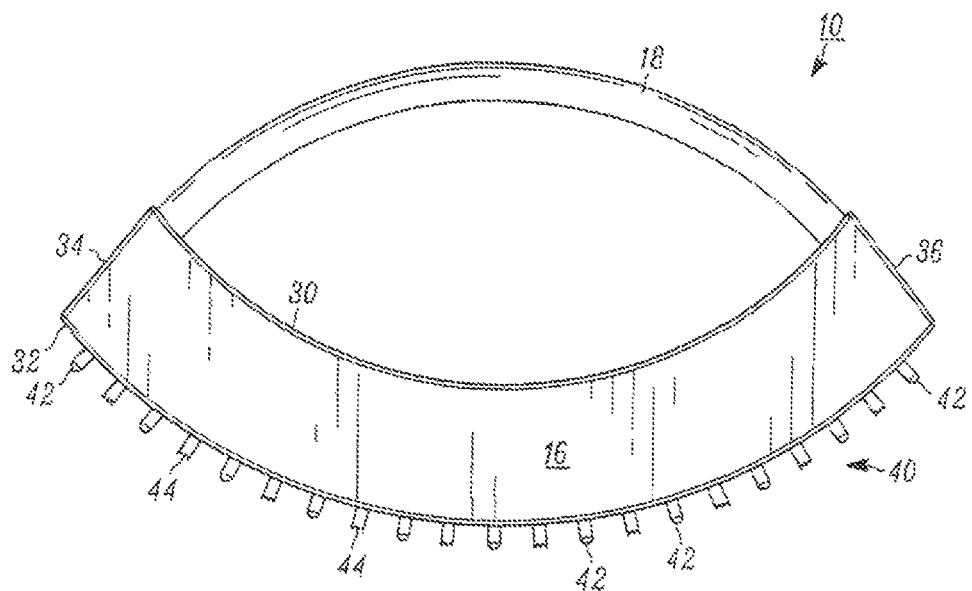
FIG. 11 is a rear elevation view of the medical testing apparatus of FIG. 8.
Figure 12:
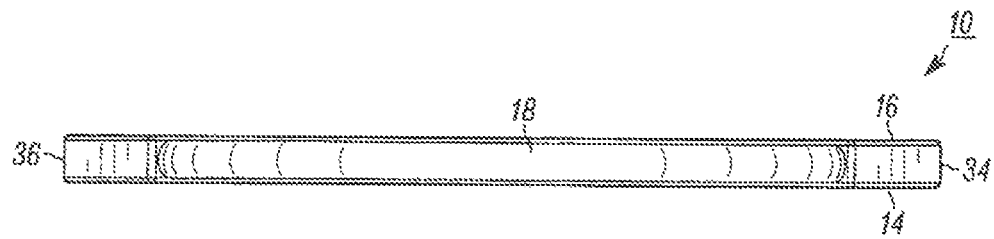
FIG. 12 is a top plan view of the medical testing apparatus of FIG. 8.
Figure 13:
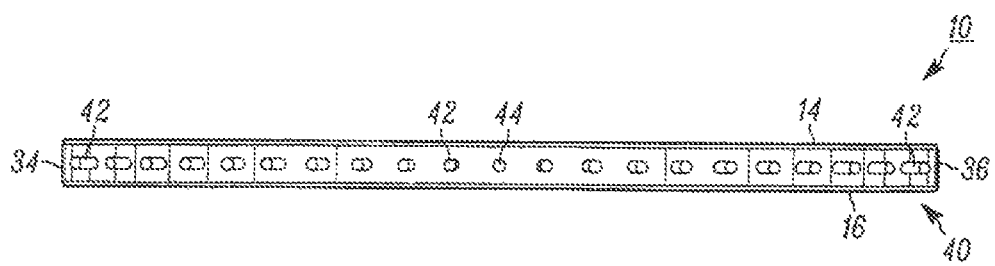
FIG. 13 is a bottom plan view of the medical testing apparatus of FIG. 8.
Figures 14, 15:
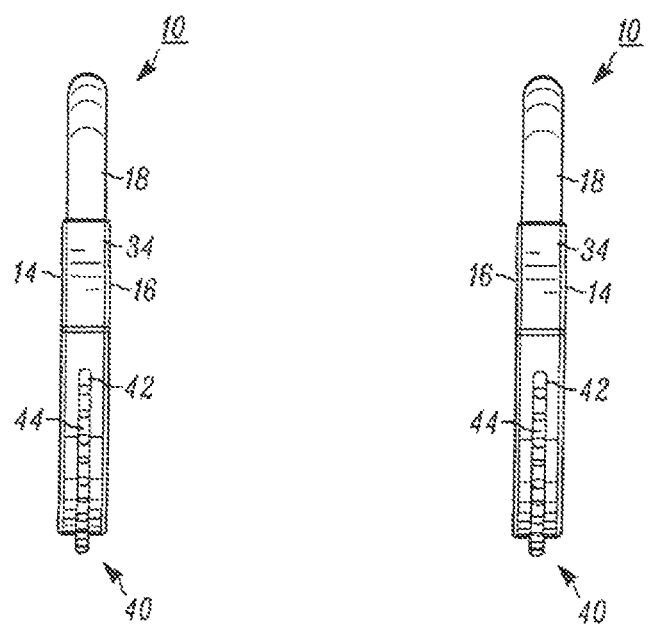
FIG. 14 is a right side elevation view of the medical testing apparatus of FIG. 8.
FIG. 15 is a left side elevation view of the medical testing apparatus of FIG. 8.

FIGS. 7A and 7B are exploded assembly views of the section view of FIG. 6. In particular, FIG. 7A illustrates the support openings 54 that extend along the middle of the arcuate upper surface 56 of the cradle 24. The arcuate upper surface 56 of the cradle 24 shares the arcuate center AC of the medical testing apparatus' arcuate rail 12. Thus, this common arcuate center AC supports or nests each of the testers 10 in the cradle 24 of the docking station.

The support openings 54 include blunt openings 58 alternating between reed openings 60. The reed openings 60 are oversized to receive test tubes 52 for removal remote filling of fluid 50. In an example embodiment, the reed openings/60 are formed into the cradle 24 like that of the blunt openings 58 and the fluid 50 is located within the openings without a test tube 52. In the illustrated example embodiment, the test tubes 52 provide sufficient clearance to avoid contact or bending of reed tips 44.

When the testing apparatus 10 is nested in the docking station 20, the reed tips 44 are sufficiently submerged in the test tubes 52 to provide capillary flow of the fluid 50 into the cavity cups 48. In the illustrated example embodiment the blunt openings 58 provide clearance about each of the blunt tips 42.

In an alternative example embodiment, the blunt openings 58 provide slight contact with the blunt tips 42 in order to provide additional support to the testing apparatus 10 in its rested or nested position on the cradle 24. In one example embodiment a different, more pliable materials such as rubber or low durometer plastics are used to form the cradle 24, further enhancing the removal and support of the testing apparatuses 10. It should be appreciated that the test tubes 52 could be placed in all the openings to provide removable fluid to both blunt and reed tips. Or alternatively, to all reed or blunt tips as illustrated in the example embodiments of FIGS. 18 and 19.

Illustrated in FIG. 7B is yet another alternative example embodiment wherein the blunt openings 58 and test tubes 52 each further comprise a pad 51 for supporting fluid such an allergen for the reed tips 44 or ink for marking the patient's skin, indentifying the location of the testing on a patient's skin or tissue. The pads 51 prevent the fluids from splashing, dripping or spilling from the recessed openings. In one example embodiment, the pads 51 are made from a fabric pad material, such as cotton, felt, or sponge.

The illustrated example embodiment of the testing apparatus 10 of FIGS. 8-15 includes a discomfort dispersal system (DDS). DDS is designed into the testing apparatus 10 to advantageously employ a neural pain gating theory by dispersing neural activation with the blunt tips 42 followed by a reed or testing tip 44, then alternating thereafter. This mitigates the discomfort level experienced by the patient in which the test or medical procedure is performed.

Pain and discomfort is further minimized in the testing apparatuses' 10 design by starting and ending with a blunt tip 42 and the curved arcuate rail 12. The curved arcuate rail 12 allows for a uniform load or force on the patient's treatment region, such as an arm or a back area. The DDS design employed by the testing device 10 includes alternating tip types, namely blunt to reed, advantageously distracting the patient from nociception of the reed or testing heads 44 when engaged by the blunt tip 42.

Figure 23:
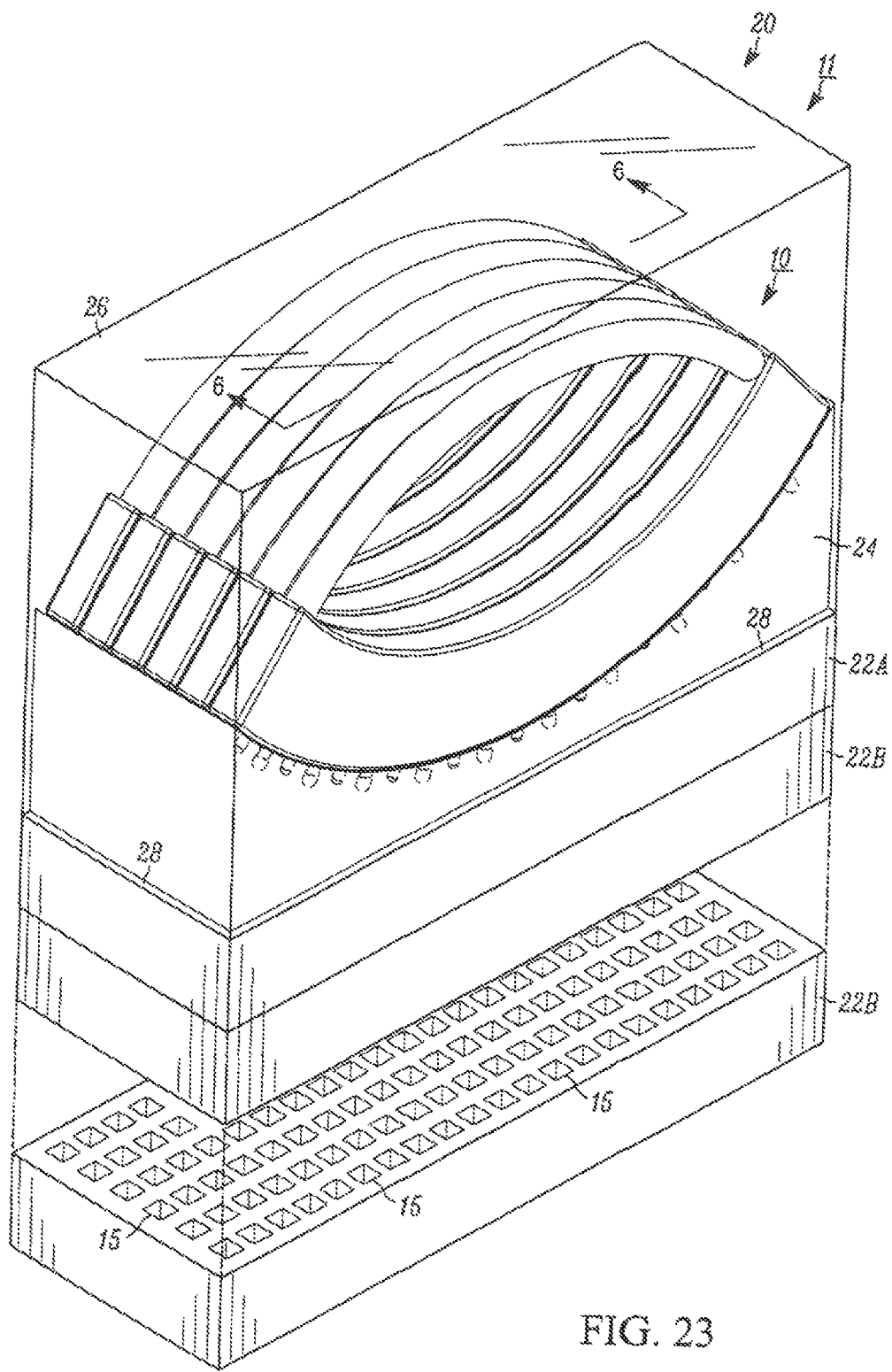
FIG. 23 illustrates a medical kit constructed in accordance with one example embodiment of the present disclosure.

Illustrated in FIG. 23 is an example embodiment of a medical kit 11 comprising a plurality of testing apparatus 10. The kit 11 further comprises a docking station 20 for supporting the testing apparatuses 10, in which the cradle 24 could provide fluid to the testing apparatuses, or alternatively, a flat well 22B is removably located within the base 22 that separates from art upper portion of the base 22A. The flat well 22B comprises a plurality of openings 15 in rows for remote filling of the openings so that the tips 42, 44 can be filled with fluid (ink, allergen, etc.) by rotating the testing device 10 through one of the rows on the well 22B.

Figure 17:
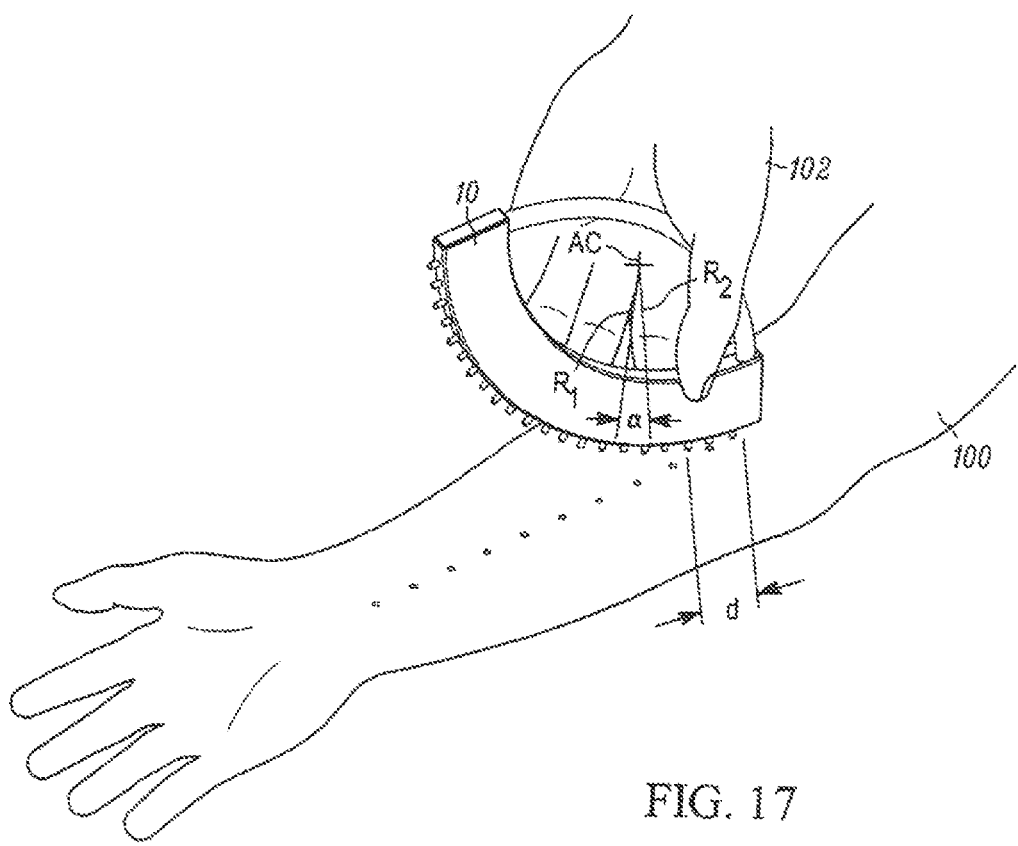
FIG. 17 is a perspective view of the medical testing apparatus in use at a finishing position on a patient in accordance with the example embodiments of the present disclosure.

Referring now to FIGS. 16 and 17 are perspective views of the medical testing apparatus 10 in use on a patient 100 in accordance with the example embodiments of the present disclosure. In particular, FIG. 16 is a perspective view of the medical testing apparatus in use at a starting position on a patient's arm and FIG. 17 is a perspective view of the medical testing apparatus in use at a finishing position on a patient's arm. It should be appreciated that the positioning and testing region of the patient could equally be positioned on any other part of the patient's body suitable for testing or medical treatment, such as, for example the patient's leg or back.

During use, the medical testing apparatus 10 is held by a medical practitioner 102, such as a nurse or doctor's fingers and thumb along spaced sides 14, 16 of the arcuate rail. The palm of the medical practitioner straddles the arcuate annular handle 18. The cavity cups 48 of reed or testing tips 44 are filled with fluid 50 such as an antigen or allergen by capillary retraction from the test tubes 52 of the cradle 24 described above.

The medical practitioner 102 then first contacts the patient's skin (in the start position of FIG. 16) with the blunt tip 42, rocking or rotating the testing apparatus 10 with uniform pressure, such that the lower arcuate surface 32 contacts the patient's skin, allowing for sufficient penetration of the alternating reed tips 44 into the patient's tissue as each reed tip passes through a normal position (i.e. substantially orthogonal or 90 degrees to the patient's skin). As the testing apparatus 10 is rotating or rocking along the patient's tissue, the procedure ends with a blunt tip 42 being normal to the patient's skin at the finished position of FIG. 17.

As further illustrated in the example embodiment of FIG. 17 the corresponding tips 42 and 44 are spaced at an angle α between tips represented by R1 and R2 from the arcuate center AC. This allows for at least one, but no more than three tips to contact the patient's skin at any given time represented by dimension d, thus minimizing discomfort and/or pain to the patient.

In the illustrated example embodiment, the reed 44 and blunt 42 tips are substantially the same overall length. In another example embodiment, the reed 44 and blunt tips extend from the arcuate lower surface 32 approximately two (2) cm, allowing for sufficient penetration of the patient's tissue, while further allowing for uniform pressure in the contact of the arcuate lower surface 32.

While the example embodiment of the testing apparatus 10 has been illustrated with ten (10) reed tips 44 and eleven (11) blunt tips 42, it should be appreciated that any number of tips could be used in an alternating combination that start and end with a blunt tip to achieve the apparatus' DDS comfort design. In addition, it should be appreciated that the medical practitioner 102 may wish to apply the agent or fluid 50 from the tester 10 by gripping and rocking the annular arcuate handle 18 as a personal preference.

Figure 24:
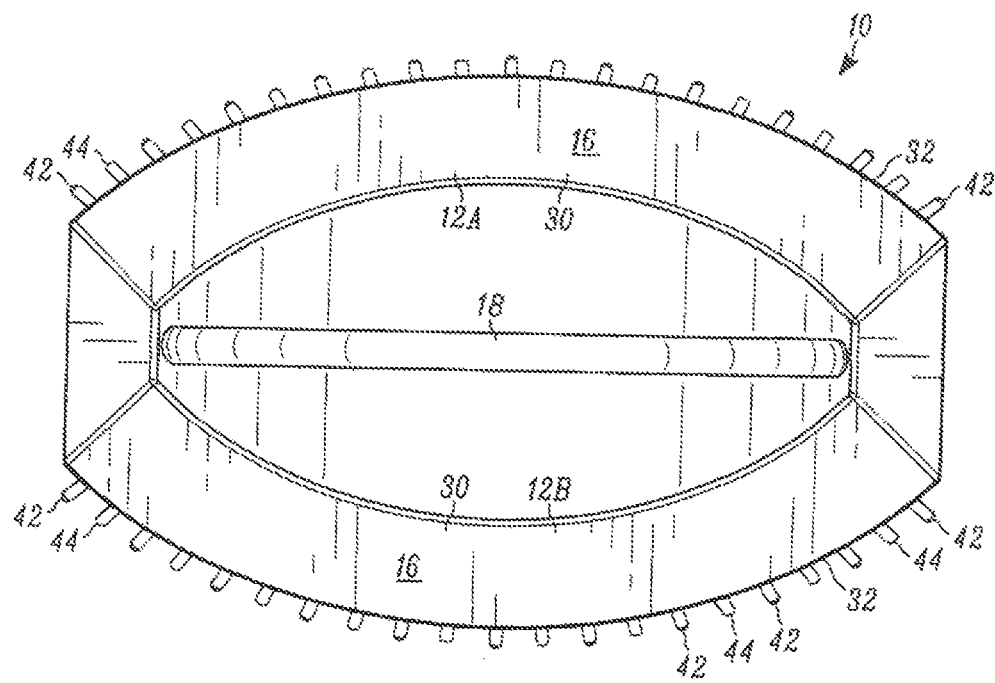
FIG. 24 is an elevation view of a testing apparatus constructed in accordance with one example embodiment of the present disclosure.
Figure 25:
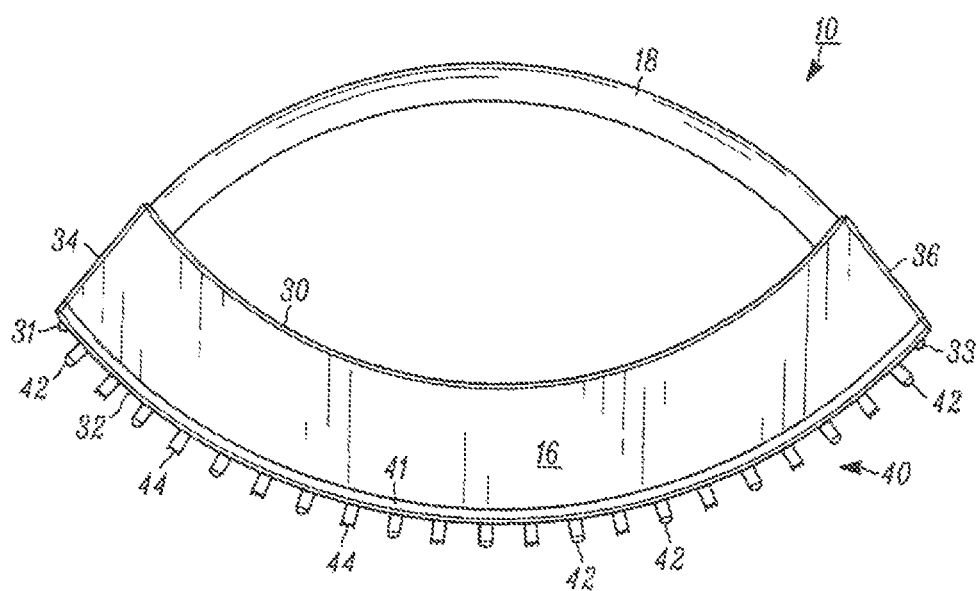
FIG. 25 is an elevation view of a testing apparatus constructed in accordance with one example embodiment of the present disclosure.
Figure 26:
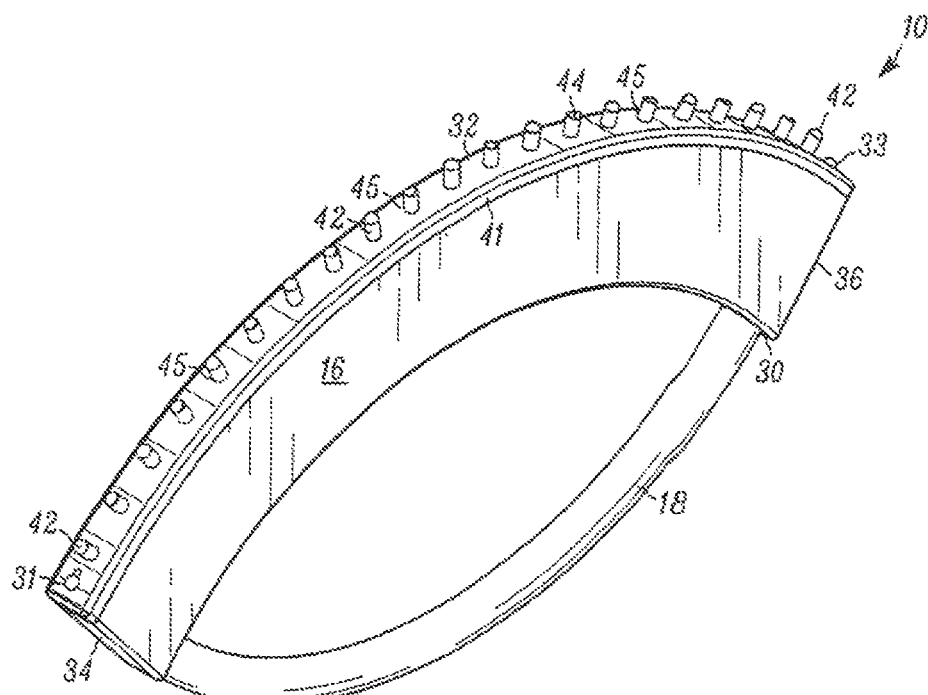
FIG. 26 is a bottom plan view of FIG. 25.
Figure 27:
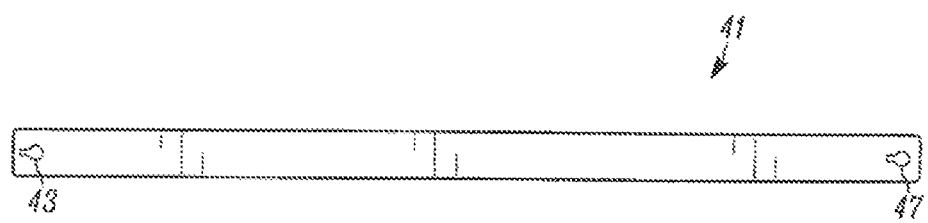
FIG. 27 is a top view of as tip strip constructed in accordance with one example embodiment of the present disclosure.
Figure 28:
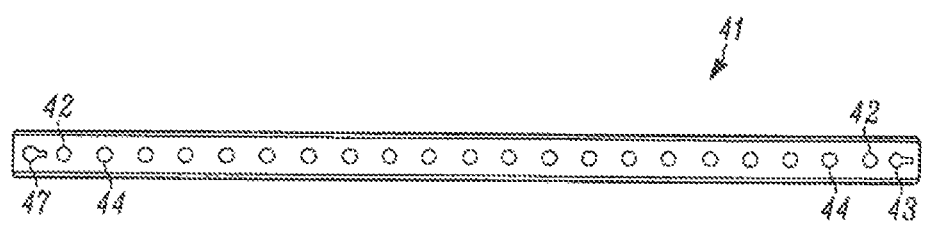
FIG. 28 is a bottom view of a tip strip constructed in accordance with one example embodiment of the present disclosure.

In the illustrated example embodiment of FIG. 24 is a double rail testing apparatus 10, including the reed tips 44 is made from molded plastic, which is both inexpensive to manufacture and allows for the disposal of the testing apparatus after a single use. In the example embodiment, the blunt tips 42 and the reed tips 44 are molded directly into the lower arcuate surfaces 32 of first rail 12A and second rail 12B. The spacing between the blunt tips 42 and reed tips 44 in the illustrated example embodiment is between one (1) and three (3) cm on the lower arcuate surface 32, allowing for sufficient viewing of reacting regions on the patient's skin. As well, the goal of the reed tips 44 is to be at least two (2) centimeters apart at the sharp points 46, where the points touch the surface of the patient's skin. In one example embodiment, no more than three (3) tips 42 and 44 collectively, touch the patient's skin at any given time, as further illustrated in FIG. 17.

The double rail testing apparatus 10 includes a handle 18 for the medical practitioner to grip that subtends the first and second arcuate rails 12A and 12B. In the illustrated example embodiment, the handle 18 is molded into the rails 12A and 12B. The practitioner may then use both rails for testing and/or marking a patient before disposing of the apparatus 10. In one example embodiment, the double rail testing apparatus 10 is provided in a kit 11, as illustrated in FIG. 23, but every other tester 10 is removed, allowing for an extra open well of fluid for the second rail 12B to be used by the practitioner.

Illustrated in FIGS. 25-28 is a medical testing apparatus of yet another example embodiment having a removable strip 41 comprising both blunt 42 and reed 44 tips. The removable strip 41 in one example embodiment is made from plastic, having first and second slots 43, 47, respectively. The slots 43, 47 allow for the passage and connection to the apparatus 10 by way of post 31, 33, as would be appreciated by one of ordinary skill in the art. In yet another example embodiment, the removable strip 41 is attached by an adhesive, fasteners, or any combination thereof. The removably connected strip 41 advantageously allows for the disposal of the tips 42, 44 after use without disposing of the entire tasting apparatus 10.

Figure 29:
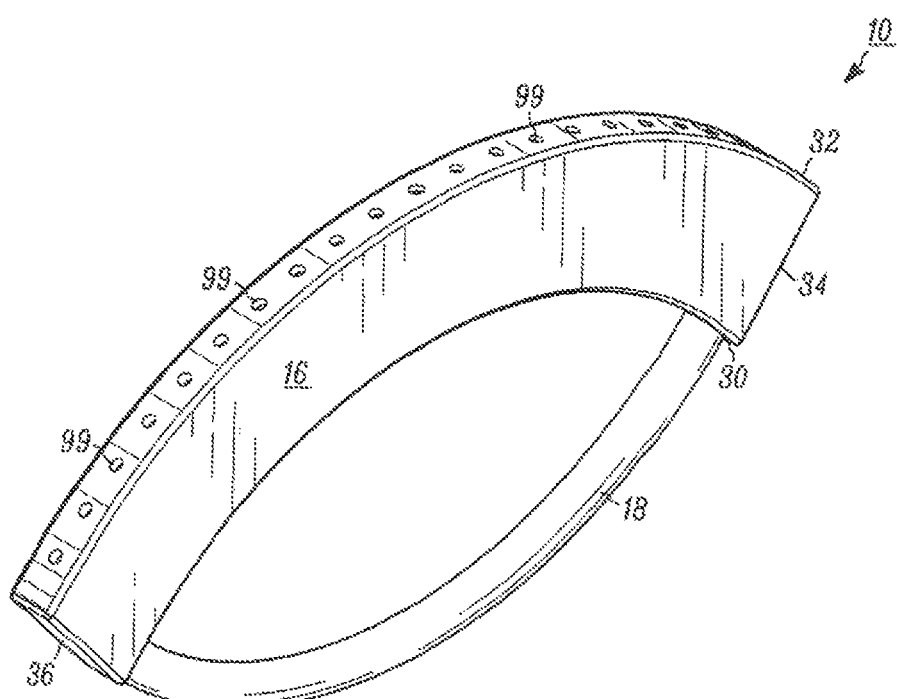
FIG. 29 is a perspective view of a testing apparatus constructed in accordance with another example embodiment of the present disclosure.

While in another example embodiment illustrated in FIG. 29, the testing apparatus 10 is similarly constructed, having openings 99 along the arcuate surface for insertion and removal, of disposable tips 42, 44. This allows the apparatus 10 to be permanent or reusable, while the tips, 42, 44, blunt or reed can be manually inserted (press-fit connection) or removed and disposable.

What have been described above are examples of the present invention. It is, of course, not possible to describe every conceivable combination of components or methodologies for purposes of describing the present invention, but one of ordinary skill in the art recognize that many further combinations and permutations of the present invention are possible. Accordingly, the present invention is intended to embrace all such alterations, modifications, and variations that fall within the spirit and scope of the appended claims.

What is claimed is:

1. A medical testing apparatus for penetrating a patient's tissue with an agent, the apparatus comprising:
    an arcuate rail having spaced first and second sides supported by upper and lower arcuate surfaces;
    an arcuate handle having first and second ends extending from said upper surface of said arcuate rail; and
    a plurality of tips extending substantially from and normally away from the lower arcuate surface, the plurality of tips comprising alternating blunt tips and reed tips, wherein a selectively removable and replaceable strip supports said plurality of reed tips, said selectively removable and replaceable strip removably coupled to said lower arcuate surface by an adhesive, said plurality of tips being supported by the surface of said removable strip.

2. The medical testing apparatus of claim 1 wherein said plurality of tips further comprises a first tip and last tip, wherein said first and last tips are blunt tips, providing neural pain gating to the patient during use.

3. The medical testing apparatus of claim 2 wherein said plurality of tips further comprises a second tip and penultimate tip, wherein said second and penultimate tips are reed tips for penetrating a patient's tissue with an agent.

4. The medical testing apparatus of claim 1 further comprising a docking station for supporting a plurality of medical testing apparatuses, the docking station comprising a cradle for holding multiple medical testing apparatuses and a lid for protecting the medical testing apparatus from evaporation or debris.

5. The medical testing apparatus of claim 4 wherein said cradle further comprises test tubes for holding agents applied to the patient through the reed tips.

6. The medical testing apparatus of claim 1 wherein said plurality of tips extend from a first end to a second end of the lower arcuate surface, the first end opposite the second end along an arced surface of the lower arcuate surface, the plurality of tips further comprises a first tip at the first end and a last tip at the second end, wherein said first and last tips are blunt tips, providing neural pain gating to the patient during use, wherein the first tip and the last tip extend a first radial distance from the arcuate surface and the reed tips extend a second radial distance from the arcuate surface, the first radial distance at least one of less than and equal to the second radial distance.

7. The medical testing apparatus of claim 1 wherein said lower arcuate surface comprises a plurality of openings for inserting and removing said plurality of tips.

8. The medical testing apparatus of claim 1 wherein said arcuate rail further comprises first and second arcuate rails, each of said arcuate rails having spaced first and second sides supported by upper and lower arcuate surfaces, said plurality of tips extending substantially from and normally away from the lower arcuate surfaces of both first and second arcuate rails.

9. A method of performing a medical testing procedure on a patient, the method comprising the steps of:
    grasping either an arcuate rail of a medical testing apparatus having spaced first and second sides supported by upper and lower arcuate surfaces or an arcuate handle of the medical testing apparatus, the arcuate handle having first and second ends extending from said upper arcuate surface of said arcuate rail;
    coupling a selectively removable and replaceable strip to the lower arcuate surface via an adhesive, a plurality of tips being supported by the surface of said removable strip; and
    contacting a patient's tissue beginning with a first tip of the plurality of tips, one or more additional tips of the plurality of tips and ending contact with a last tip, wherein the plurality of tips extend substantially from and normally away from the lower arcuate surface, wherein said plurality of tips extend from a first end to a second end of the lower arcuate surface, the first end opposite the second end along an arced surface of the lower arcuate surface, the first tip at the first end and the last tip at the second end, wherein said first and last tips are blunt tips,
    providing neural pain gating to the patient during use, the first tip and the last tip extend a first radial distance from the arcuate surface and the reed tips extend a second radial distance from the arcuate surface, the first radial distance being at least one of less than and equal to the second radial distance.

10. The method of claim 9 further comprising the step of contacting said patient's tissue with said additional tips wherein said additional tips comprise alternating blunt tips and reed tips.

11. The method of claim 10 further comprising the step of contacting said patient's tissue with said plurality of tips wherein said alternating blunt tips and reed tips provide neural pain gating to the patient during the application of the medical testing procedure, wherein the blunt tips extend the first radial distance from the arcuate surface.

12. The method of claim 10 further comprising the step of contacting said patient's tissue with said plurality of tips wherein a second tip and a penultimate tip are reed tips for penetrating a patient's tissue with an agent.

13. A medical kit used for contacting a patient's tissue with a fluid, the medical kit comprising;
    a medical testing apparatus having:
        an arcuate rail comprising spaced first and second sides supported by upper and lower arcuate surfaces;
        an arcuate handle having first and second ends extending from said upper surface of said arcuate rail; and
        a plurality of blunt and reed tips coupled to a selectively removable and replaceable strip, said selectively removable and replaceable strip removably coupled to said lower arcuate surface by an adhesive, said selectively removable and replaceable strip being supported by the surface of said removable strip the plurality of blunt and reed tips extending substantially from and normally away from the lower arcuate surface in a spaced relationship;
    a base having a cradle for supporting at least one medical testing apparatus, the cradle further comprising a well having a plurality of recesses for storing and supplying fluid to at least one of said blunt tips and said reed tips for contacting a patient's skin during use.

14. The medical kit of claim 13 wherein said well is substantially linearly shaped.

15. The medical kit of claim 13 wherein said well is substantially arcuately shaped.

16. The medical kit of claim 13 wherein said recesses within said well further comprises a pad for supporting fluid within each respective recess.

17. A medical testing apparatus for releasing a fluid to a patient's tissue, the apparatus comprising:
an arcuate rail having spaced first and second sides supported by upper and lower arcuate surfaces;
an arcuate handle having first and second ends extending from said upper surface of said arcuate rail; and
a plurality of tips comprising a combination of reed and blunt tips, the tips extending substantially from and normally away from the lower arcuate surface, the plurality of tips being in a spaced relationship about said lower arcuate surface wherein said plurality of tips extend from a first end to a second end of the lower arcuate surface, the first end opposite the second end along an arced surface of the lower arcuate surface, the plurality of tips further comprises a first tip at the first end and a last tip at the second end, wherein said first and last tips are blunt tips, providing neural pain gating to the patient during use, wherein the first tip and the last tip extend a first radial distance from the arcuate surface and the reed tips extend a second radial distance from the arcuate surface, the first radial distance being at least one of less than and equal to the second radial distance; and
a selectively removable and replaceable strip, said selectively removable and replaceable strip removably coupled to said lower arcuate surface by an adhesive, said plurality of tips being supported by the surface of said removable strip.

18. The medical testing apparatus of claim 17 wherein said plurality of reed tips extend from said lower arcuate surface to a radial distance greater than a radial distance formed by said blunt ends such that said reed tips always contact a patient's tissue before blunt tips adjacent to said reed tips.

19. The medical testing apparatus of claim 17 further comprising a finger or thumb support molded into and projecting from said handle at one of said first and second ends.

20. The medical testing apparatus of claim 17 wherein said arcuate rail further comprises first and second arcuate rails, each of said arcuate rails having spaced first and second sides supported by upper and lower arcuate surfaces, said plurality of tips extending substantially from and normally away from the lower arcuate surfaces of both first and second arcuate rails.

* * * * *